(12) United States Patent
Yi

(10) Patent No.: US 9,091,620 B2
(45) Date of Patent: Jul. 28, 2015

(54) PREPARING BLOOD SMEARS ON A FIBER SURFACE

(71) Applicant: Chen Yi, Boxborough, MA (US)

(72) Inventor: Chen Yi, Boxborough, MA (US)

( * ) Notice: Subject to any disclaimer, the term of this patent is extended or adjusted under 35 U.S.C. 154(b) by 0 days.

(21) Appl. No.: 13/867,717

(22) Filed: Apr. 22, 2013

(65) Prior Publication Data

US 2013/0309711 A1    Nov. 21, 2013

Related U.S. Application Data

(60) Provisional application No. 61/636,403, filed on Apr. 20, 2012.

(51) Int. Cl.
*G01N 1/28*    (2006.01)

(52) U.S. Cl.
CPC .................................... *G01N 1/2813* (2013.01)

(58) Field of Classification Search
None
See application file for complete search history.

(56) References Cited

U.S. PATENT DOCUMENTS 3,678,151 A * 7/1972 Horonick et al. ............ 435/40.5
5,846,422 A * 12/1998 Ditter et al. .............. 210/500.41
2003/0175153 A1* 9/2003 Anaokar et al. ................ 422/56

OTHER PUBLICATIONS

ALQEP, Blood Film Staining Effects, May 2004: retrieved from the internet: http://www.cpsa.ab.ca/Libraries/pro_qofc_alqep_critiques/Blood_Film_Staining_Effects_Educational_Document.pdf?sfyrsn=0.*
Ceelie et al., J. Clin. Pathol (2006) vol. 60, pp. 72-79.*

* cited by examiner

*Primary Examiner* — Allison Fox
*Assistant Examiner* — Yvonne Pyla
(74) *Attorney, Agent, or Firm* — Coats and Bennett, PLLC

(57) ABSTRACT

The present application discloses methods and apparatus for preparing blood film or smear samples on a fiber surface, staining the test sample, and generating digital cell images of the films or samples for classification and review. The techniques disclosed herein replace conventional microscope slides with fibers when preparing blood film test samples. Using fibers to prepare blood test samples facilitates automation and integration of the various processes involved in hematology analysis. The techniques disclosed herein can be used to improve the accuracy and efficiency of hematology analysis.

7 Claims, 12 Drawing Sheets

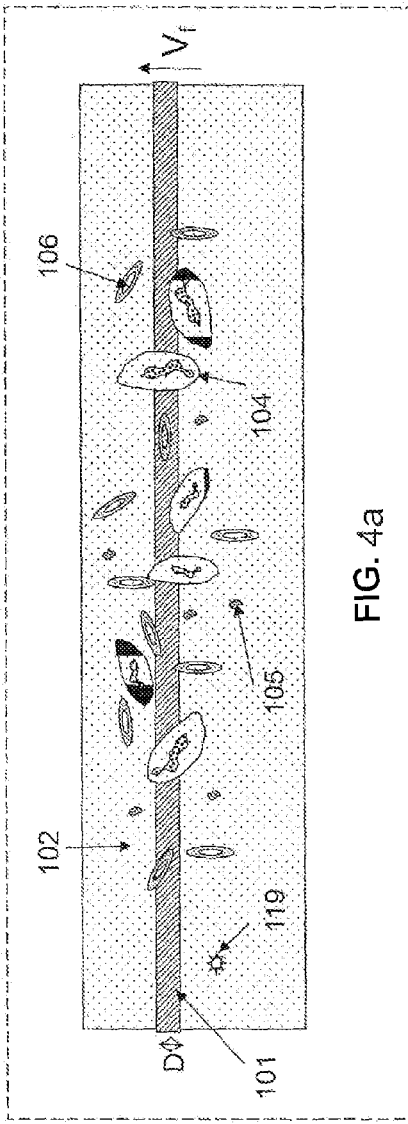
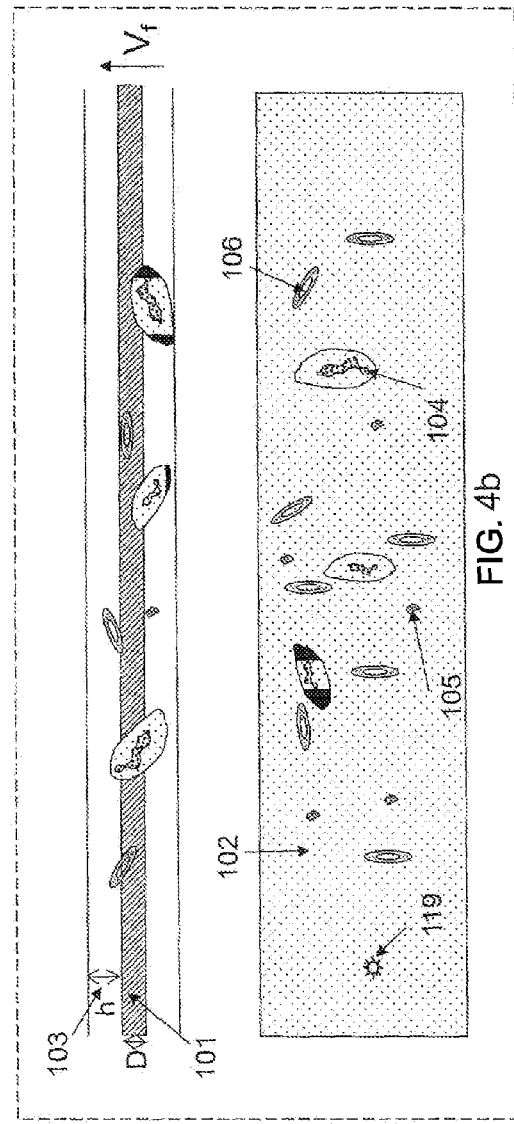
FIG. 4a
FIG. 4b

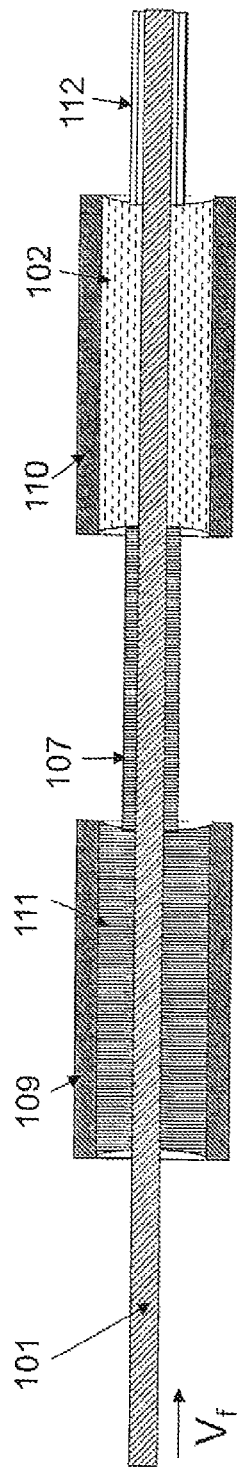
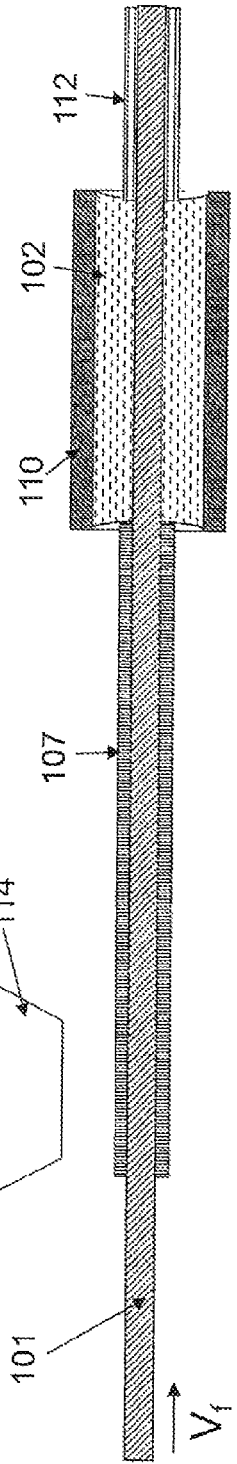
FIG. 6a
FIG. 6b

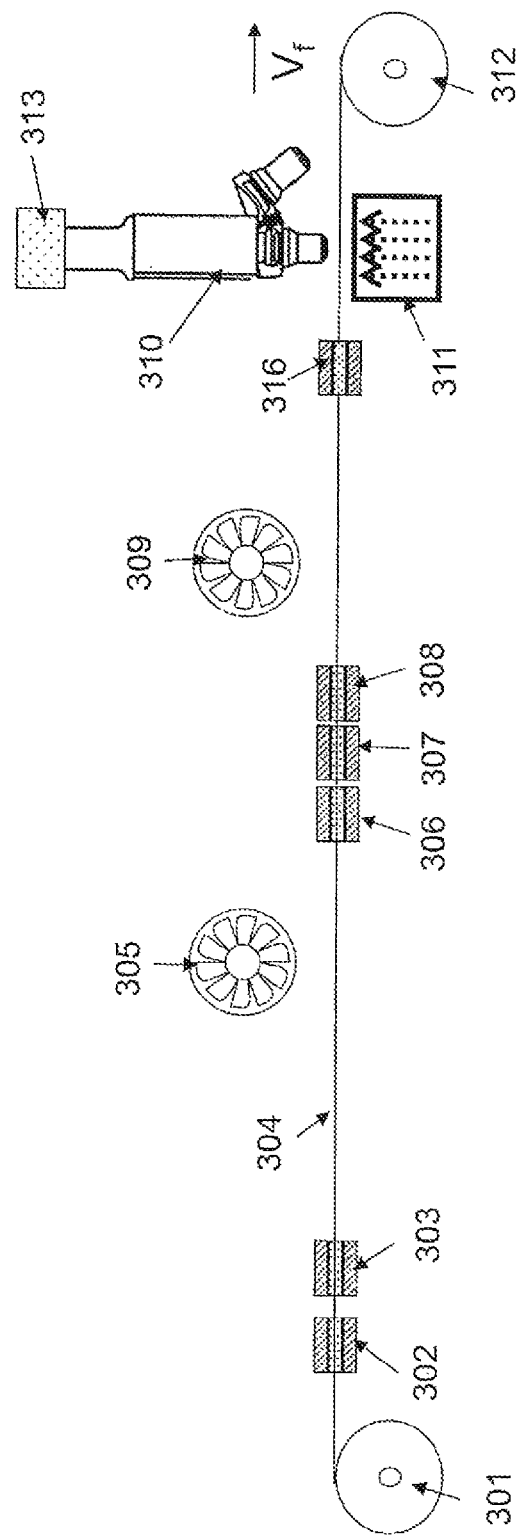
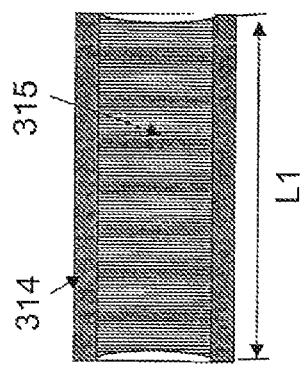
FIG. 12b
FIG. 12a

PREPARING BLOOD SMEARS ON A FIBER SURFACE

PRIORITY CLAIMS

The present application claims priority to U.S. Provisional Application No. 61/636,403 filed on Apr. 20, 2012.

TECHNICAL FIELD

The present application relates generally to methods and apparatus for preparing blood samples. More specifically, the present application relates to methods and apparatus for preparing blood films or blood smears on a fiber surface, staining the blood cells, and generating digital blood cell images for classification and review.

BACKGROUND

Evaluation of human blood cells is a valuable medical procedure. For example, detection of morphological changes in certain cells or abnormal counts of certain types of cells can lead to diagnoses of certain diseases. But blood cell evaluation is a labor-intensive procedure that involves various instruments, such as centrifuges, spectrophotometers, counting chambers with etched grids, and stained wedge smears of blood. Also blood cell evaluation requires that various reports on red cell indices, white cell counts, white blood cell differentials, and platelet counts be collected.

Hospitals usually rely on automated instruments to perform testing on blood smears. Most automated hematology instruments employ one of the following two methods to measure blood cells. The first method uses an impedance technique to measure the number of blood cells in a test sample. During a test, as blood cells pass through an aperture in a single file, the momentary reduction in conductivity caused by each passing blood cell is detected and counted. The second method relies on optical means. During a test, hydrodynamic focusing technique is used to force the diluted blood cells in the test sample to pass through a flow cell/chamber one by one. As the cells pass through the flow chamber, light beams are focused on the blood sample. As the light beams are scattered by the blood cells in the sample, both forward and side scattered light is analyzed to study the sizes, numbers, and granularities of both white and red cells in the test sample.

Automated blood cell analysis can be performed with little or no human intervention. And the entire analysis only lasts for several minutes. But, according to Patrick C. J. Ward[6], automated hematology is not a perfect technology even 40 years after its invention. Identifications of irregular cells, such as immature red or white blood cells, blast cells, circulating lymphoma cells, or atypical lymphocytes, still require a hematologist. Usually, when detecting an irregular cell, an automated device would flag the test for further review by a hematologist. According to a 2006 study conducted by the College of American Pathologists, of the 263 laboratories surveyed, an average of 29% of the automated CBC (complete blood count) results required a manual review. The percentage of test results requiring a manual review could increase dramatically in certain pathology studies. Further, in cases where abnormal lymphoid populations are present, most automated hematology analyzers cannot distinguish between small lymphoid blasts, circulating small lymphoma cells, and normal lymphocytes, and often fail to flag these conditions for further diagnosis.

In today's blood tests, examinations by technicians to identify white blood cell differentials and morphology of white blood cells, red blood cells and platelets are essential. During a manual slide review, a technician well trained in morphologic hematology can distinguish abnormal red cell shapes induced during a staining process from pathologically abnormal red cells. Other challenging tasks that call for a manual blood slide review include identifying fragmented cell forms indicating angiopathic hemolytic anemia (e.g., those associated with disseminated intravascular coagulation) and detecting the presence of immature red and white blood cells and blasts, an indicator of myelodysplastic syndromes or acute leukemia.

Further a manual slide review requires blood films to be prepared in advance, which is a challenging task as well. Wedge blood smear, cover glass smear and spun blood smear methods are three methods commonly used to prepare blood films. The wedge blood smear method can be used in both manual and automated tests. In the wedge blood smear method, a drop of blood is placed about 0.5 inch from one end of a first slide. A second spreader slide is then used to spread the blood into a thin film. The second spreader slide is at about 30°-45° angle relative to the first slide. The blood film generated by the spreader slide sliding along the first slide has a variable thickness. Generally, the part of the film farthest away from the starting point will be too thin, which may cause morphological alterations. The part of the film close to the start of the push will be too thick for microscopy examination. A technician or an automatic slide inspector must find the optimal area for inspection. Also in a wedge blood smear test, the quality of the blood smear depends on a number of factors, for example, the technique used, the viscosity of the blood, the blood smear drying process, the staining process and the environment (such as temperature and humidity). Reference U.S. Pat. No. 5,779,982 describes an automatic blood smear preparing apparatus.

The second method is the cover glass method. In a cover glass method, a small drop of blood is first spread using capillary action generated between two cover glasses. The cover glasses are then pulled apart smoothly in a horizontal plane. However, the cover glass slides used in a cover glass method are often small and difficult to label. In addition, the cover glass method involves higher biohazard risk than the wedge blood smear method. The cover glass method is generally not recommended and has become almost obsolete.

The third method is the spun blood film method. The spun blood film method has been described as an alternative to the wedge blood smear method. It can be automated just as the wedge blood smear method. In a spun blood film method, the blood cells in a test sample are spread over a glass using centrifugal forces. The blood cells form a monolayer that can be stained before microscopic examination. When properly prepared, the morphological condition of all cell types in a spun blood film is generally excellent, although care has to be taken to avoid the formation of smudge cells. However, the instruments used to generate spun blood films, the so-called "cell spinners", are hazardous because of the formation of droplets and blood aerosols. Also the interior of a cell spinner is almost always contaminated with blood from previous tests, which may cause cross contaminations among test sample and is a potential source of biohazard. Prior art U.S. Pat. Nos. 4,305,722 and 4,016,828 describe a method of preparing blood films on a microscope slide using the spun blood film method.

Conventionally, an automatic blood smear preparation method uses microscope slides as the substrate for carrying the blood film. Microscope slides are a convenient media for manual examination because they have already been used with manual microscopes for other purposes and they can be stored for later review. However, microscope slides take up valuable lab storage space and it is often a tedious task to retrieve a stored slide for review. As such, conventional microscope slides often seem inefficient and outdated.

In hematology analyzers that are currently available, up to 30% of blood test samples are flagged by automatic hematology analyzers for need of human review. Also processes of smear making, smear staining, and blood cell image recording are carried out separately on conventional microscope slides. There is a need for improvements on current hematology analyzers.

SUMMARY

The present application describes using fiber substrates to carry blood films as test samples. Compared to conventional microscope slides, the disposable substrates are smaller in size and have a shape that is more suitable for use with automated analyzers and digital image technologies. With a smaller stained surface area, fiber substrates require less blood and fewer reagents. Compared to microscope slides used for conventional blood smears, it is easier to obtain a blood smear with a uniform cell density on the surface of a fiber and most of the blood smear generated on a fiber substrate is usable. Digital imaging devices are used to record or generate blood smear images. Those images can be made smaller in size to match digital imaging devices, and can be digitally recorded for current and later reviews. The fiber substrates can be stored or discarded after testing.

The recorded digital images can be analyzed using sophisticated pattern recognition software. For example, using pattern recognition techniques, white blood cells can be differentiated from other cell types and counted. In addition the instrument can flag abnormal red blood cells and platelet morphology and can perform morphological review of red blood cell and platelet images.

In some embodiments, an apparatus for generating a sample smear on a fiber surface comprises a sample holder for holding a test sample, a piece of fiber for using as a substrate, a microscope for observing the test sample, and a device for pulling the fiber through the sample holder and under the microscope. As the fiber is pulled through the sample holder, a sample smear is imprinted or created on the fiber. As the fiber is pulled under the microscope, the sample smear is observed. In some embodiments, the microscope may further comprise a digital camera for recoding an image of the sample smear as the fiber is pulled under the microscope. In some embodiments, the apparatus may comprise one or more solution holders. Each holder may be used to hold a fixing agent, staining solution or washing solution. In other embodiments, the apparatus may further comprise one or more fans. The fans may be used to dry the sample smear or other solutions used on the fiber. In some embodiments, the fiber may be immersed into the test sample to create the sample smear. In other embodiments, the test sample may be sprayed or dropped on the fiber to create the sample smear. Yet in some embodiments, the apparatus further comprises a device for analyzing the recoded image, another device for generating a signal when a pre-defined criterion is met. The pre-defined criterion may include detecting certain medical conditions present in the sample smear.

In some embodiments, a method for generating a sample smear on a fiber surface comprises generating a sample smear on the fiber surface when the fiber surface is moved through a holder holding a test sample, and analyzing the sample smear under a microscope as the sample smear is moved under the microscope. In some embodiments, analyzing the sample smear under the microscope comprises recoding an image of the sample smear.

The methods and apparatus disclosed in the present application require less blood, less time to prepare and stain cells, and less waiting time. The methods and apparatus disclosed in the present application can accommodate different staining procedures and allow for more accurate and precise CBC testing. Finally as disclosed in the present application, the apparatus for making and staining blood smear samples and automated microscopic analysis (both during recording and reviewing) is easy to manufacture and can be easily incorporated with current automated hematology analyzers.

DESCRIPTION OF DRAWINGS

FIGS. 4a-4b illustrate a forth exemplary embodiment of making blood film test sample on a fiber surface.

FIGS. 6a-6b illustrate a first exemplary method for pre-coating a fiber and create a blood film on the fiber.

FIG. 12a is a schematic diagram illustrating an apparatus for making a blood film sample on a fiber surface and staining the cells in the film sample with Romanowsky stains (May Grunwald Giemsa, Wright Giemsa, and Wright Stains), and recording the digital images of the cells by the camera mounted on the microscope.

FIG. 12b is a detailed view of 302, 303, 306, 307, 308, and 316 shown in FIG. 12a.

DETAILED DESCRIPTIONS

The present disclosure relates to methods and apparatus for preparing blood films on a fiber surface. One aspect of the present invention involves making a blood film on a fiber surface, controlling the thickness (cell density) of the blood film, and controlling the blood cell type distribution on the surface of the fiber. Blood films using techniques disclosed in the present application have the same or similar attributes as those prepared on conventional microscope slides. Those attributes include color, transparency, cell density, cell morphology, distribution of different cells (such as the ratio of white bloods, red blood cells and platelets).

The techniques disclosed herein replace conventional microscope slides with fibers in preparation for blood film test samples. Using fibers to prepare blood test samples facilitates automation and integration of the various processes involved in hematology analysis. The various processes may include making and staining blood smears, recording blood cell images, and reporting test results. The test results may include white blood cell differential, red blood cell morphology, platelet morphology, red blood cell indices and other parameters.

Hematology blood smear application is just one example of many uses of the new and innovative methods disclosed herein for collecting particles from a liquid using a piece of fiber. It will become obvious to those skilled in the art that this new technology holds advantages in other applications such as urine analysis or other body fluid analysis, cancer cell collection from a liquid or collection of other types of cells suspended in liquid, etc.

The following sections describe different embodiments of preparing blood smears on a fiber surface. Different techniques are described for controlling the thickness and cell density of a blood film formed on a fiber surface and for controlling the distribution of different cell types collected from blood onto the surface of a fiber. Also disclosed in the following sections are the apparatus for performing the process of blood smearing and staining on a fiber surface and the process of recording cell images.

Coating Process

Figure 1:
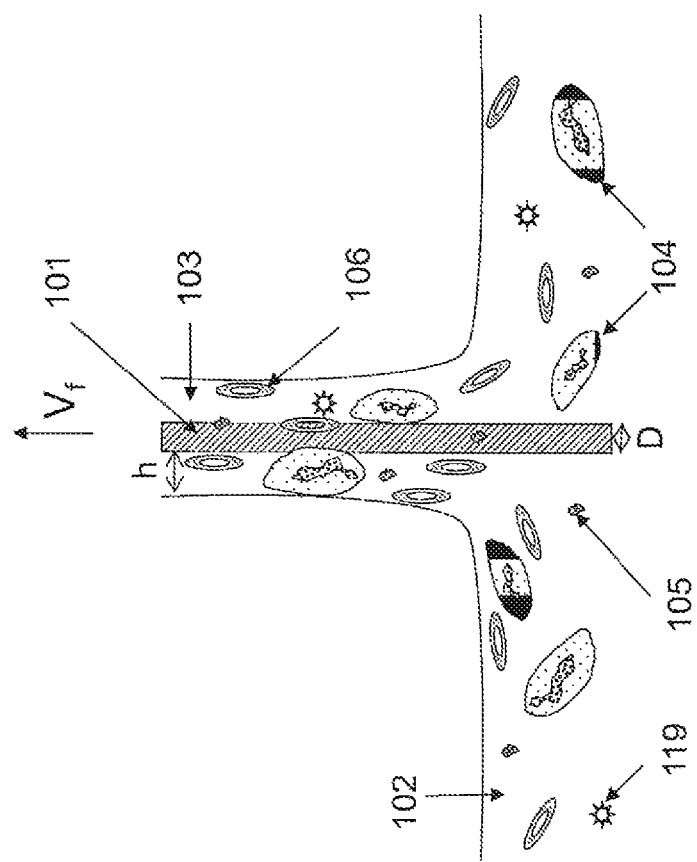
FIG. 1 illustrates a first exemplary embodiment of making a blood film test sample on a fiber surface.

FIG. 1 illustrates a first embodiment of preparing a blood test sample using a piece of fiber in accordance with the innovative technologies disclosed herein. FIG. 1 depicts a pool or droplet of blood 102. Inside the blood pool 102, there are white blood cells 104, red blood cells 106, platelets 105 and other particles 119. Examples of the other particles 119 may include bacterial, virus, debris, or other components normally seen in whole blood.

In FIG. 1, a piece of fiber 101 is pulled through the blood pool 102 at a velocity $V_f$ for a predefined distance. In some embodiments, instead of being pulled through, the fiber 101 is dipped into the blood pool 102 and immersed in the blood pool for a period of time $t_1$ before being pulled out of the blood pool 102. The velocity $V_f$ with which the fiber 101 is pulled out of or through the blood pool 102 can be adjusted to ensure that a layer 103 of blood cells coated on the fiber 101 is an optimal monolayer. $V_f$ can be set to a constant or a variable. A constant draw speed $V_f$ will normally result in a uniform layer 103 of blood cells on the surface of fiber 101. A variable draw speed $V_f$ will generate a layer of blood 103 with variable thicknesses h on the fiber 101. Sometimes coating with variable thicknesses may be desirable, for instance, to allow a technician to locate the optimum spot on the coated fiber 101, similar to the conventional wedge method.

Figure 2A:
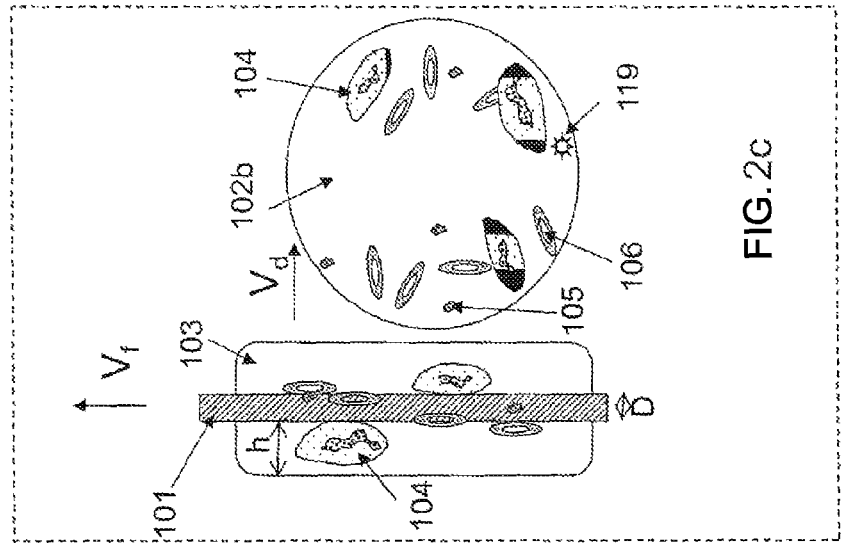
FIGS. 2a-2c illustrate a second exemplary embodiment of generating a blood film test sample on a fiber surface.
Figure 2B:
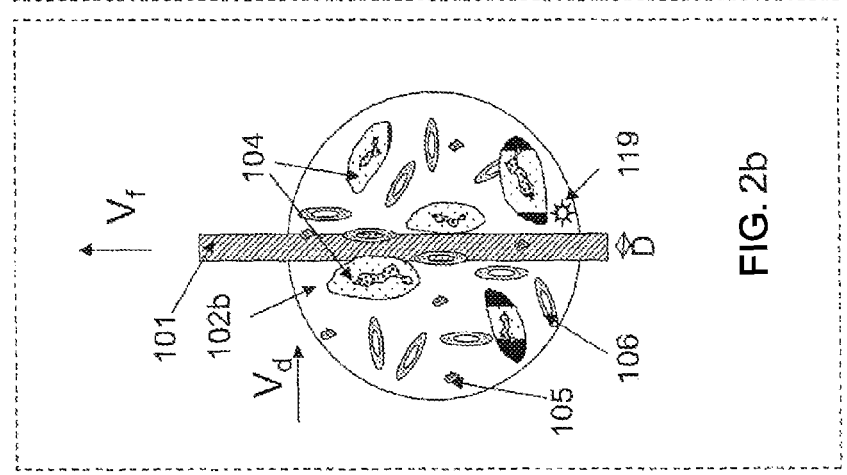
Figure 2C:
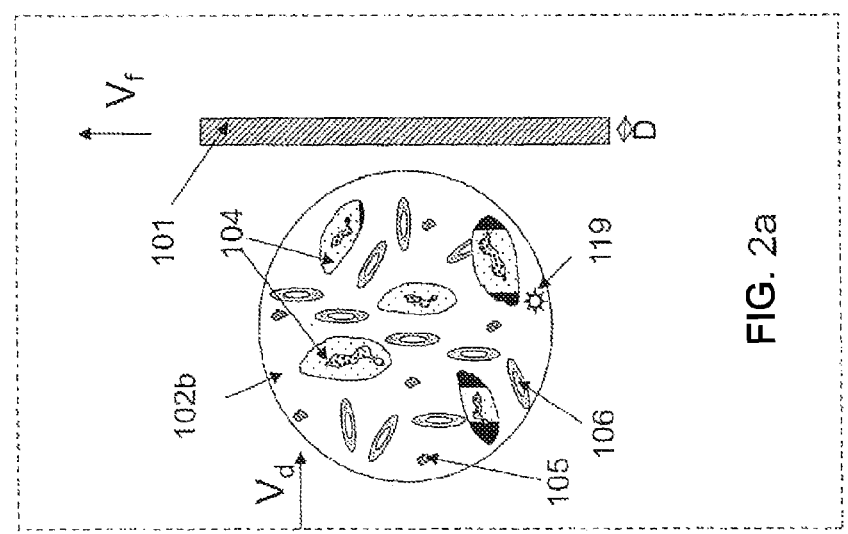

FIGS. 2a, 2b and 2c illustrate a second embodiment of preparing a blood sample on a fiber surface. A drop of blood 102b is applied to the fiber 101 with a speed $V_d$ as shown in FIG. 2a. Only one drop of blood 102b is illustrated in FIGS. 2a, 2b, and 2c for demonstration purpose. The same principle can be applied to multiple drops of blood too. The blood drop or drops 102b can be applied by pipette, nozzle, print head, spraying or other dispensing methods. The blood drop 102b falls through the fiber 101 as shown in FIGS. 2b and 2c. A portion of the blood drop 102b breaks away from the fiber 101 as shown in FIG. 2c. But a thin layer of blood 103 with thickness h is coated on the fiber 101. In some embodiments, depending on the speed $V_d$ of the blood drop 102b and the size of the drop 102b, the entire drop 102b may be retained on the fiber 101 to form the blood layer 103.

In FIGS. 2a, 2b and 2c, the fiber 101 is also shown as moving with a speed $V_f$ to control the thickness h of the blood layer 103 similar to those shown in FIG. 1. Alternatively, the fiber 101 can move in an opposite direction of $V_d$ shown in FIG. 2C. The fiber 101 can also vibrate back and forth in a stream of blood at velocity $V_d$.

Figure 3B:
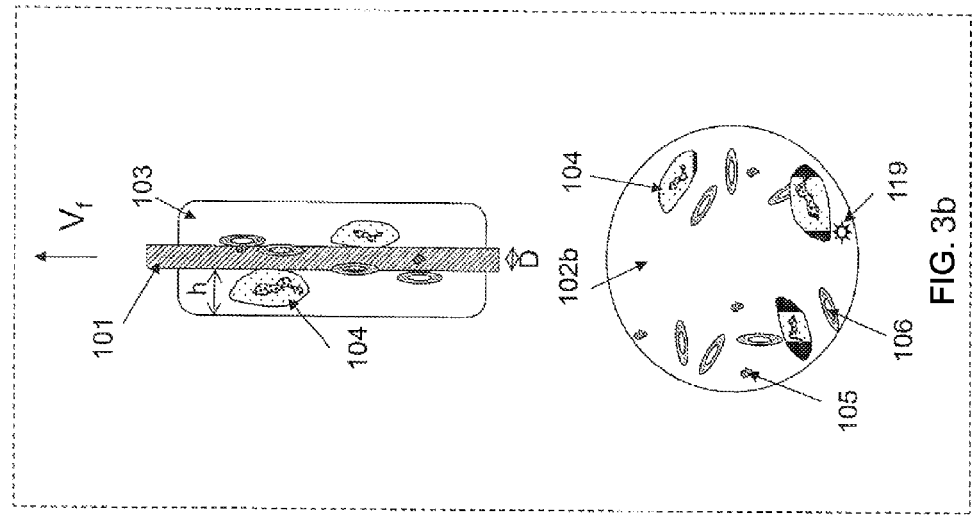
FIGS. 3a-3b illustrate a third exemplary embodiment of making a blood film test sample on a fiber surface.
Figure 3A:
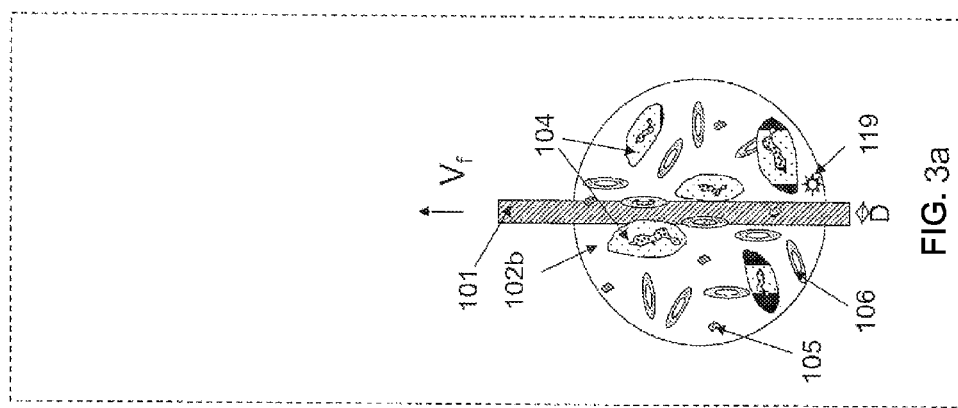

FIGS. 3a and 3b illustrate a third embodiment of preparing a blood sample on a fiber surface. Only one drop of blood 102b is shown in FIGS. 3a and 3b for demonstration purpose. The same techniques can be applied to multiple drops of blood as well. As shown in FIGS. 3a-3b, the blood drop or drops 102b are applied to the fiber surface 101. The blood drop or drops 102b can be applied by pipette, nozzle, print head, spraying or other dispensing methods. In FIG. 3a, the fiber 101 is shown to have a diameter smaller than the diameter of the blood drop. But the fiber 101 can be larger than the diameter of blood drop 102b at the position where the blood is applied. In some embodiments, a small mechanic device, not shown in the figures, can be attached to the fiber 101 where the blood 102b is applied to provide a footing area for the blood drop 102b. After the blood drop 102b is applied to the fiber 101, the fiber drawing speed $V_f$ may be increased suddenly to allow the blood drop to move along the fiber 101 opposite to the direction of $V_f$ through an inertial force. This creates a thin layer of blood 103 on the fiber surface 101 as shown in FIG. 3b.

FIGS. 4a and 4b illustrate a fourth embodiment of making blood smear on a fiber surface. As shown in FIG. 4a, the fiber 101 is dipped into a blood pool or drop 102. After a period of time $t_1$, the fiber 101 is pulled out as shown in FIG. 4b with a speed of $V_f$. A layer of blood 103 with a thickness h is coated on the fiber surface 101. The angle between the speed $V_f$ and the fiber 101 can vary from zero to ninety degree.

Controlling Cell Density

In a blood film made for hematology study, the best area for microscopy is where red blood cells form a single layer and barely touch each other. The desired density of red blood cells is about 2 cells for every 256 $\mu m^2$ area. Other blood tests may need either thinner or thicker blood films. For example, a blood smear sample prepared for malaria diagnostic analysis needs be thicker than 2 cells per 256 $\mu m^2$. Thicker blood films allow a technician to examine a larger number of red cells for the presence of parasites. And parasites, even in low density, can be more readily identified in thick films. Thin blood films are preferred when examining the morphology of parasites and determine species.

Figure 5:
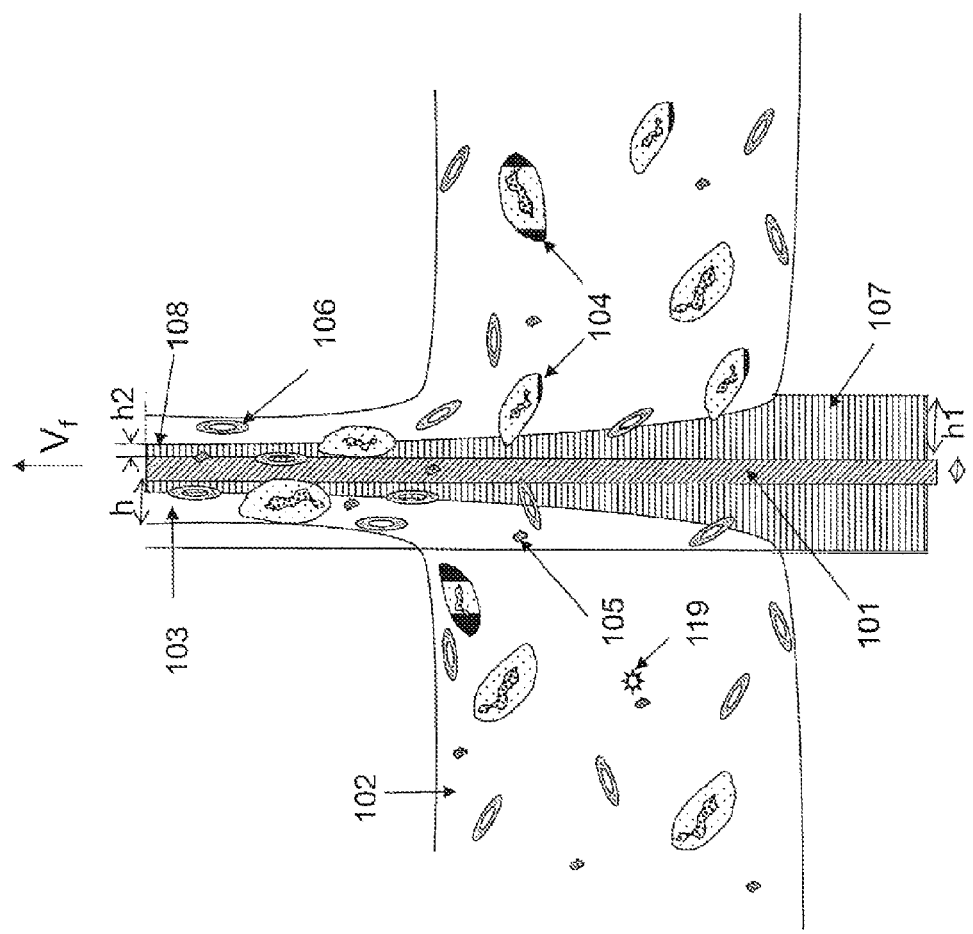
FIG. 5 illustrates a pre-coating step during a process of making a blood film test sample on a fiber surface.

According to the first embodiment of the invention, the thickness h of layer 103 in FIG. 1 can be varied by adjusting the speed $V_f$. Therefore the cell density coated on the surface of fiber 101 can be controlled. Normally, the slower the $V_f$ is, the thinner the blood layer 103 becomes. When $V_f$ reaches, for example, more than several meters per second, an increase of $V_f$ will not increase the thickness h of the blood layer 103. This relationship between $V_f$ and h also holds for the embodiments described in FIGS. 3a-3b and 5.

The thickness h of the layer 103 can also be controlled by controlling the diameter D of the cross section of the fiber 101 (see FIGS. 1-5). The thickness of the blood layer h decreases as the fiber diameter D decreases.

FIGS. 6a and 6b show exemplary pre-coating and coating processes in preparation of a fiber to generate blood smear samples on the fiber surface. In FIG. 6a, the fiber 101 is first pre-coated with solution 111 in the solution holder 109. After leaving the holder 109, the fiber 101 is coated with a thin layer 107 of the solution 111. The fiber 101 enters the blood sample holder 110, which contains blood sample 102. As the fiber 101 comes out of the blood sample holder 110, the fiber is coated with a layer 112 of blood sample. In some embodiments, a nozzle 114 (shown in FIG. 6b) is used to apply the solution 111 to pre-coat the fiber 101 with a layer 107 of the solution 111. The solution 111 can also be applied to the fiber by a pipette or other solution applying devices. The process of coating the fiber 101 with blood sample illustrated in FIGS.

Figure 9:
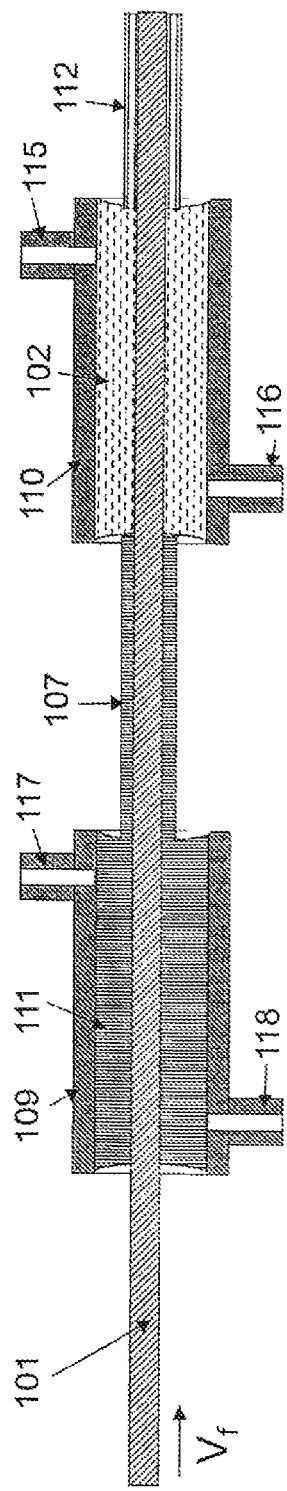
FIG. 9 illustrates a process of replenishing reservoirs of a pre-coating solution and blood sample.

6a and 6b is similar to the process illustrated in FIG. 1. FIG. 9 shows a method of refreshing the solutions in the holders by adding inlet port 117 and outlet port 118 to avoid using contaminated, or overly-evaporated (e.g., overly concentrated) solutions. This refreshing method can also be applied to blood, fixing agent, staining solution and washing solution.

Figure 7:
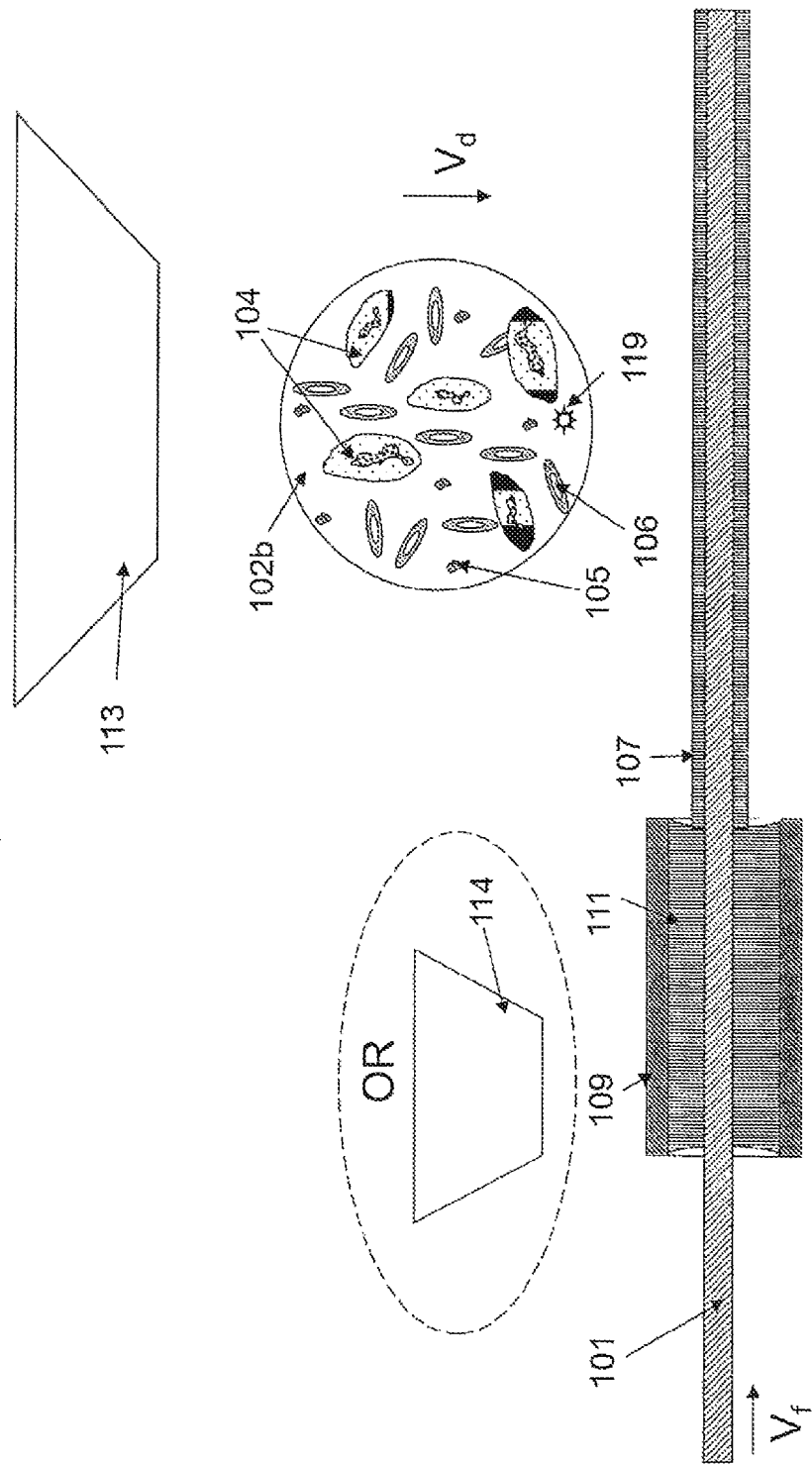
FIG. 7 illustrates a second exemplary method of pre-coating a fiber and making blood films on the fiber.

FIG. 7 shows another exemplary process of pre-coating and coating a fiber to make blood smear sample on the fiber surface. The pre-coating process in FIG. 7 is similar to that in FIGS. 6a and 6b. The coating process is similar to that illustrated in FIG. 2.

Figure 8:
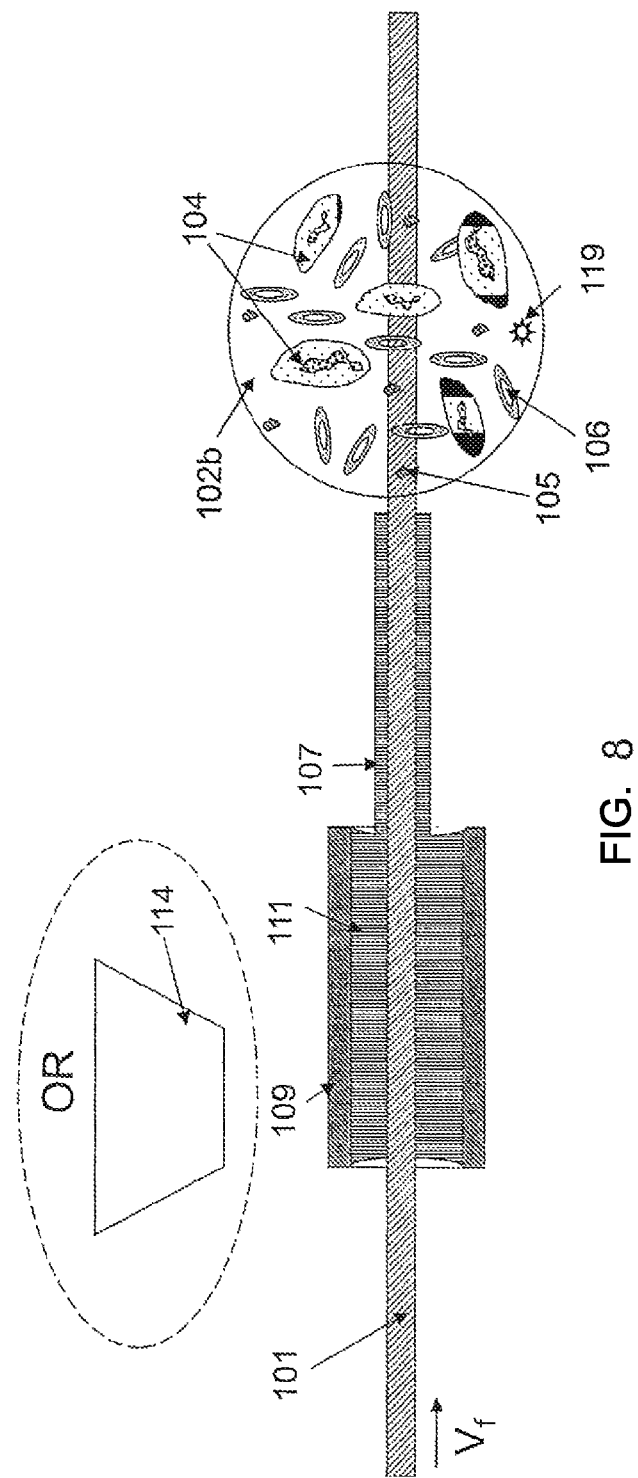
FIG. 8 shows a third exemplary method of pre-coating a fiber and making blood films on the fiber surface.

FIG. 8 shows yet another exemplary process of pre-coating and coating a fiber to make blood smear sample on the fiber surface. The pre-coating process is similar to the pre-coating process illustrated in FIGS. 6a and 6b. The coating process is similar to that illustrated in FIG. 3. In a further aspect, the blood sample 102 can be diluted with an isotonic solution 111 before being applied to the fiber to further decrease the final cell density on the fiber surface 101 in any of the embodiments described herein.

The solution 111, for example, can be made with 9.9 grams NaCl per liter of solution. The balance of the solution is DI (deionized or distilled) water. Such solution provides a proper osmotic balance for cells. Other isotonic solutions known to those skilled in the art can also be used. It should be noted that other solutions can also be used along with the solution 111 without affecting the characteristics of the test sample, such as the morphology of the cells, the distribution of different cell types on the fiber, and the molecules in the affinity of the blood cells.

Figure 11A:
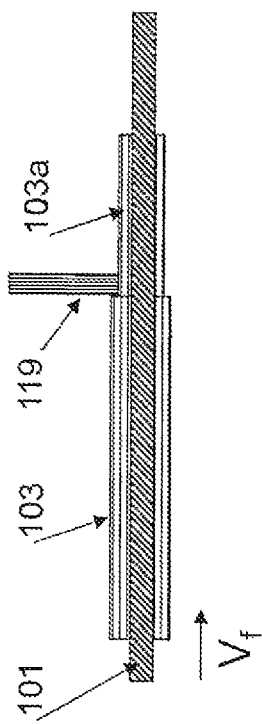
FIGS. 11a-11d illustrate a method of using a wedge to make a blood film sample on a fiber surface.
Figure 11D:
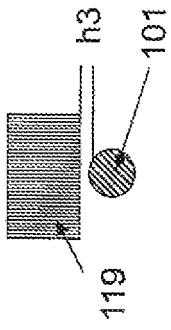
Figure 11C:
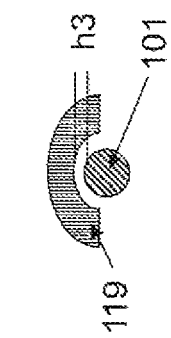
Figure 11B:
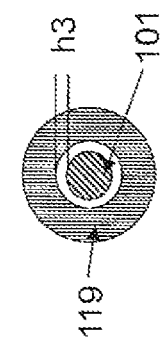

FIGS. 11a, 11b, 11c and 11d illustrate a method of using a wedge 119 to control the thickness of the blood smear 103 on the fiber surface 101. Examples of different shapes of the wedge 119 are shown in FIGS. 11b, 11c and 11d. The original blood layer 103 becomes thinner after passing wedge 119 at a speed $V_f$. The speed $V_f$ may be constant or variable. In FIG. 11b, the wedge 119 is made of one co-centric ring. The fiber 101 is completely surrounded by the wedge 119. In FIGS. 11c and 11d, the fiber 101 is partially surrounded by the wedge 119. The shapes of the wedge 119, a circle in FIG. 11b, an arc in FIG. 11C and a block in FIG. 11d, are set forth as examples. The distance h3 between the fiber 101 and the wedge 119 shown in FIGS. 11b, 11c and 11d can vary from zero to the thickness of blood layer 103.

To ensure that the percentage of each type of cells in the blood sample remains the same when the blood sample is coated onto the surface of the fiber, the thickness of the blood film or smear coated on the fiber is critical. Normally, a thicker layer of blood sample is needed for larger cells, such as white blood cells. A layer of 5 μm coated blood or more may be needed for those large cells. The above described blood dilution method and precoating method are suitable for use to coat a thicker layer of blood onto the fiber surface and still keep the cell density sufficiently low enough to be within the required ranges.

In FIG. 1, when the fiber 101 is vibrating during the process, the density of the coated blood will be relatively higher than without vibration. When the vibration is strong enough, a dense monolayer of red blood cells may be coated onto the fiber 101. In the dense layer of blood cells, most of the red blood cells touch adjacent cells. The vibration of the fiber 101 can be achieved by pulling the fiber with a stepping motor. Each movement of the stepper motor (such as the advance of each step of the stepper motor) may cause a vibration of the fiber 101. Other methods to cause vibrations in the fiber can be used. Instead of the fiber 101, the blood sample holder 110 in FIGS. 6a and 6b can be also vibrated to achieve similar effects. Also rotating the fiber 101 along an axis in one direction (or backward and forward) produces similar effects on the density of the cells.

The following examples are provided to further illustrate the present invention and should not be construed as limiting the present invention in any way.

(1) Example 1

The relationship between the cell density and the drawing speed $V_f$ in the first embodiment is described in FIG. 1.

The fiber used in this example is obtained from Paradigm Optics. The fiber is 500 μm in diameter and is made of polystyrene. In one experiment, bovine blood with EDTA as anticoagulant is used. The setup is illustrated in FIG. 6a. The pre-coating device 109 is not used. A variable speed motor is used to pull the fiber at different velocities, $V_f$. The measurement results of cell density are given in Table 1. It should be noted that when a mechanical vibration is introduced to holder 110 and/or fiber 101, the cell density may not follow the relationship shown in Table 1. For example, the cell density measured at speed $V_f$ of 0.9 cm/sec with vibration is still very similar to the cell density measured at the speed $V_f$ of 2.4 cm/sec without vibration.

TABLE 1

Relationship of cell density and drawing speed $V_f$

| test | $V_f$, cm/sec | Cell density, # of cells per $16 \times 16$ μm$^2$ |
| --- | --- | --- |
| 1 | 2.4 | 4.6 |
| 2 | 1.5 | 2.1 |
| 3 | 0.9 | 1.1 |

(2) Example 2

Effects of Pre-coating on Cell Density

The fiber used in this experiment is made by Paradigm Optics. It is 500 μm in diameter and is made of polystyrene. The setup is illustrated in FIG. 6a. The pre-coating device 109 is included. A variable speed motor is used to pull the fiber at different velocities, $V_f$. The pre-coating solution 111 is made of 9.9 grams NaCl per liter of De-Ionized (DI) water. The coating solution provides a proper osmotic balance for cells. As indicated by the test result, when the speed $V_f$ is set to 2.4 cm/sec, without pre-coating (i.e., the device 109 is not used), a monolayer of cells is formed at the fiber surface with a sufficient high density such that adjacent red blood cells touch each other. At the same speed of 2.4 cm/sec, with pre-coating, a monolayer of cells are formed at the fiber surface. And the adjacent red blood cells don't touch each other. With pre-coating, the cell density is less than half of the cell density that can be achieved without pre-coating.

(3) Example 3

Effects of Dilution on Cell Density

The fiber used in this example is again from Paradigm Optics. It is 500 μm in diameter and is made of polystyrene. Bovine blood with EDTA as anticoagulant is used as blood sample. The setup is illustrated in FIG. 6a. The pre-coating device 109 is not used. A variable speed motor is used to pull the fiber at different $V_f$. The diluent solution 111 is blood serum and the ratio of whole blood to serum is 1:1. The measurement results of cell density are given in Table 2.

TABLE 2

Effects of dilution on cell density

| Test | Diluent used | $V_f$, cm/sec | Cell density, # of cells per $16 \times 16\ \mu m^2$ |
|---|---|---|---|
| 1 | No | 1.5 | 2.1 |
| 2 | Yes | 1.5 | 1.1 |

(4) Example 4

Effects of Fiber Diameter on Cell Density

The fibers used in this example are purchased from TheFiberOpticStore.com. They are 750 μm and 250 μm in diameter. The core of the fibers is PMMA and coated with Fluorinated Polymer. Bovine blood with EDTA as anticoagulant is used as test sample. The setup is illustrated in FIG. 6a. The precoating device 109 is not used. A variable speed motor is used to pull the fiber at different $V_f$.

TABLE 3

Effects of fiber diameter on cell density

| Test | Fiber diameter, μm | $V_f$, cm/sec | Cell density, # of cells per $16 \times 16\ \mu m^2$ |
|---|---|---|---|
| 1 | 750 | 1.5 | 6.0 |
| 2 | 250 | 1.5 | 0.26 |

In the present invention, cells or other particles under investigation in liquid are coated onto a surface of a fiber. The fiber material may be made of metal, glass, nylon, polystyrene, PMMA, or other plastic materials, but preferably polystyrene or glass. Other natural fibers can also be used. Optical fiber with or without cladding is also a good candidate due to its intrinsic high quality. It has almost no air bubbles and no optical impurities. Also, its diameter tolerance is high and its surface is clean.

Figure 10:
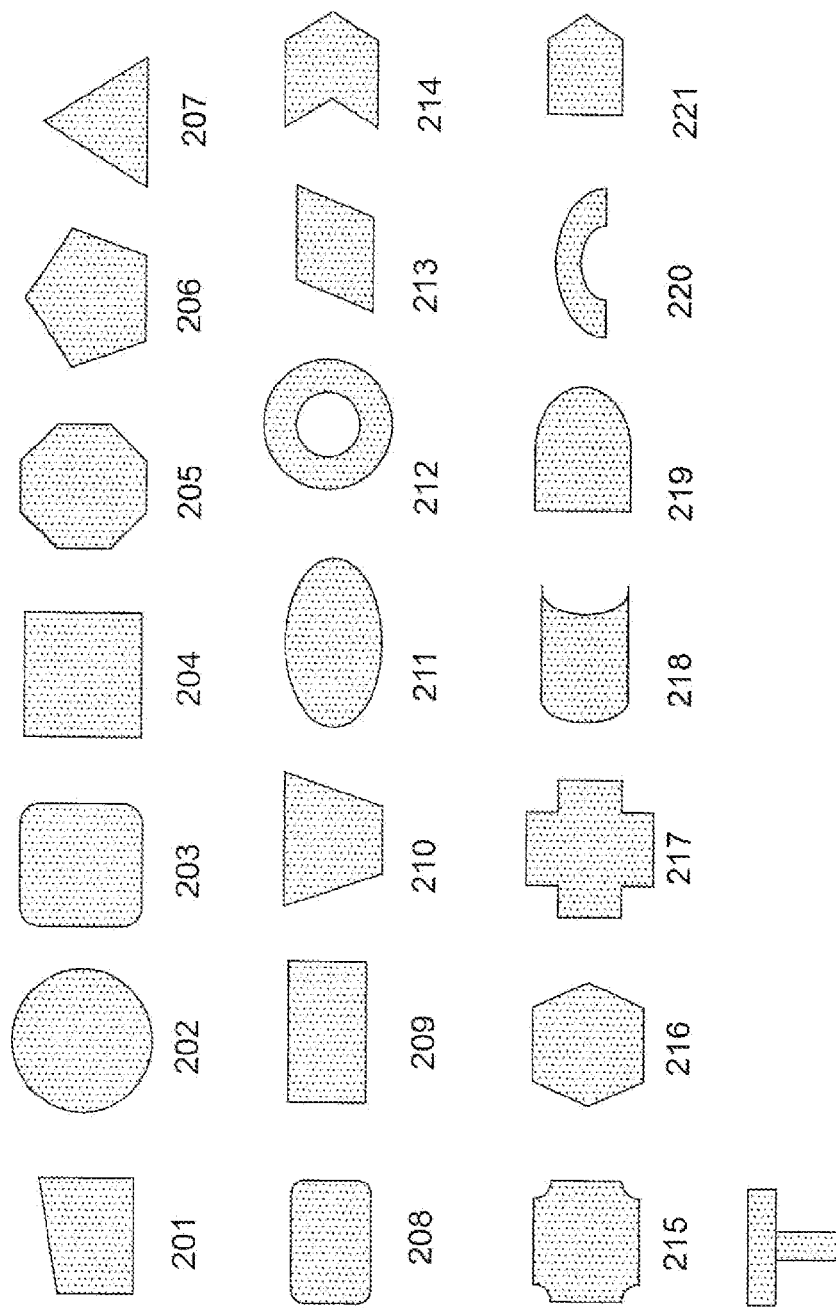
FIG. 10 illustrates exemplary cross sectional geometry of different fibers used as substrates carrying blood samples.

In the present invention, the cross section of the fiber used for blood sample preparation can be of different geometric shapes as shown in FIG. 10. The different shapes shown in FIG. 10 are set forth as examples and should not be construed as limiting. In some embodiment, the preferred geometric shapes of the cross section of the fiber are oval, round, square and rectangular. In some embodiments, the preferred width of the fiber cross section is between 10-3000 microns for hematology applications, with a width between 200-1000 microns being most desirable.

In addition, a fiber with a shape shown as 214, 217, 220, or 222 in FIG. 10 has a varied surface that can be used to generate a coated layer of varied thickness. When different cell densities are desirable in one blood test, such as those thin and thick blood films needed in a malaria blood smears test sample, a fiber with a varied surface can provide different cell densities in a single coating event. A test sample having different cell densities provides a better opportunity of obtaining a cell density optimal for a particular blood test, requiring less control for the thickness of the blood coating.

In the implementations described above, blood samples are used to coat the fiber surface. The methods and apparatus disclosed herein are also suitable for preparing other samples. In one implementation, urine test samples are generated using a piece of fiber. Urinary samples often contain red blood cells, white blood cells, epithelial cells, bacterial cells and other particles. These cells and particles can be coated onto the fiber surface and be counted and/or identified using the techniques disclosed herein.

In another implementation, a cell culture solution can be coated onto a fiber surface. The particles and floating cells such as dead cells in the cell culture solution that are coated onto the fiber surface can be tested and analyzed using the techniques disclosed herein.

In yet another implementation, drinking water samples can be prepared using a piece of fiber. Cryptosporidium, Giardia, and other particles in a water sample that coated to the fiber surface can be counted or analyzed using the techniques disclosed herein.

The methods and apparatus disclosed herein can also be applied to body fluids such as bone marrow fluid, pleural fluid, cerebrospinal fluid, bile, breast milk, vaginal secretion, semen, saliva, mucus, aqueous humour, endolymph and perilymph, and peritoneal fluid.

Also the methods and apparatus disclosed herein can be used for air sample analysis. Particulates such as pollen found in air samples can also be coated onto a fiber that is pre-coated with oil or some other matrix. Charging the fiber with either positive or negative charges can also pull particulates from an air sample.

The method and apparatus disclosed herein can be used to coat liquids or particulates in air or other gases onto a fiber surface. The molecules, particles, bacterium, viruses, blood cells and other contents in the liquid or gas under investigation can be coated onto the surface of the fiber as well. These particles can be viewed or detected using a microscope or other acoustic or optical device.

FIGS. 12a-12b describe a specific embodiment of the present invention. The apparatus in FIG. 12 can be used for casting a blood smear on a fiber, cell staining and digitizing (and interpreting) an image.

FIG. 12a is a schematic diagram illustrating an exemplary apparatus for making a blood smear on a fiber surface, staining the cells with Romanowsky stains (May Grunwald Giemsa, Wright Giemsa, and Wright Stains), and recording the images of cells by a camera mounted on the microscope.

FIG. 12b is a detailed view of 302, 303, 306, 307, and 308 in FIG. 12a. The solution holder 314 comprises a top and bottom piece. The material used to construct the holder 314 can be metal, glass, plastic, wood, ceramic, rubber or other nature materials, but preferably polystyrene or some type of plastics. The liquid in the holder 314 can be either the pre-coating solution (if at position 302), test sample (position 303), fixing agent (position 306), stain solution (position 307), or washing solution (position 308). The length of the holder is shown as L1.

Fiber 304 originates from the spool 301 and is pulled by the roller 312. The roller 312 is driven by a stepper motor to keep the fiber moving with a speed of $V_f$. At the start of the process, the fiber 304 is pulled through the holder 302 containing a preconditioning solution (for example, the solution 111 in FIG. 6a). After the fiber 304 goes through the holder 302, the precondition solution is coated on the surface of the fiber 304. Then the pre-coated fiber 304 goes through the holder 303 containing a blood test sample. As the fiber leaves the blood holder 303, a layer of blood is coated on the surface of the fiber 304. The fan 305 is used here to dry the blood coating on the fiber 304. The time it takes for the blood test sample on the fiber 304 to dry before reaching the holder 306 is estimated to be around several minutes. If Romanowsky stain is used, the holder 306 may contain methyl alcohol. After the fiber 304 passes through the holder 306, the blood cells on the surface of the fiber 304 will be fixed. The fiber 304 with the fixed cells enters the holder 307 containing Romanowsky stain solution. The cells are stained while the fiber passes through the holder 307. The holder 308 contains DI water or washing buffer solutions to wash the stained cells on the fiber. After leaving the wash holder 308, the cells on the fiber is dried by fan 309. As the last step, the cells on the fiber 304 go through a microscope 310. A digital camera 313 mounted on the microscope 310 records the images of sample to be analyzed.

In the example shown in FIG. 12a, the speed $V_f$ of the fiber is independently controlled. By adjusting the speed of the fiber, a desired cell density can be achieved in the blood sample coated on to the fiber 304 at the holder 303. The fiber speed $V_f$ should also be adjusted to ensure that the cells on the fiber 304 are properly fixed at the holder 306, stained at the holder 307 and washed at the holder 308 with optimal timed intervals in between. In one example, 0.5 minute is allocated for the fixing process at the holder 306, 5 minutes for the staining process at the holder 307 and 1 minute for the washing process at the holder 308.

In yet another example, more staining holders such as 307 and washing holders such as 308 can be added for more complicated staining procedures. One example of the more complicated procedure is the staining process in which Pappenheim's panoptic stain is used. After getting blood smeared onto the fiber with the blood holder 303 as previous described, the blood is dried by the fan 305. The cells are fixed with Methanol at the holder 306. The cells (using the holder 307) are then stained with May-Grunwald eosin-methylene blue solution for 3 minutes. The cells are then counter-stained (with one more holder 307) with a diluted May-Grunwald eosin-methylene blue solution for about 3 minutes. In the next step, the stained cells are re-stained (with another holder 307) with a Giemsa solution and then diluted in a Giemsa solution (with another holder 307) for about 15-20 minutes. Afterwards, the cells are washed with DI water in the holder 308 and be dried by the fan 309. An optical oil holder 316 is used to apply oil to the blood smear for oil objective lens just before the fiber entering the microscope 310. Finally, the images are taken by the camera 313 mounted on the microscope. The light source 311 is for illumination of the blood smear for microscope 310. As described in the previous sections, the fiber speed $V_f$ is controlled to achieve the required exposure time for different staining solutions. Also, holder length L1 in FIG. 12b can be used to control the exposing time, too. Alternately a combination of $V_f$ and the length of holder L1 can be used to control the exposure time for the cells to different staining solutions used during the procedure.

In yet another implementation, reticulocytes are imaged with Heilmeyer's stain. The process includes the following steps. First, pre-mix a 1% brilliant cresyl blue solution (in physiologic saline) with a whole blood sample. An exemplary ratio may be 1:1. Incubate the mixture for about 15-20 minutes. Apply the mixture that contains the stained blood sample to the holder 303. As described in the previous implementation for Romanowsky stains, the fiber is coated with blood samples at the position 304 and dried at the position 305. Then the cells are fixed at the position 306. At the position 307 there is an optional staining or counter-staining process. A process known as Giemsa counter-staining can be used for preparing high quality blood samples. The fiber can also move directly into the washing holder 308. The cells on the fiber can be dried by the fan 309 as the last step in preparation. The fiber 304 may be pulled through the microscope 310 with a camera mounted at the microscope 313 to record the images of blood cells.

In yet another implementation, Kleihauer-Betke Stain can be used to detect the presence of fetal hemoglobin in red blood cells. To accommodate this complicated procedure, the solution holders and fans as shown in FIG. 12a may need to be rearranged. An example of the new sequence is: holder 302 (preconditioning solution), holder 303 (blood coating), holder 306 (80% ethyl alcohol fixing), holder 308 (DI water washing), holder 309 (air drying), holder 308 (buffer washing), holder 308 (DI water cleaning), holder 307 (Ehrlich hematoxylin staining), and holder 307 (0.1% erythrosine counter staining solution). The detailed procedure is described by H. Loffler.

Although the description above contains many details, these should not be construed as limiting the scope of the invention but merely as providing illustrations of some of the presently preferred embodiments of this invention. Therefore, the scope of the present invention is understood to fully encompass other embodiments which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present disclosure. Moreover, it is not necessary for a device or method to address each and every problem sought to be solved by the present invention for it to be encompassed by the present disclosure.

A number of embodiments of the invention have been described. Nevertheless, it will be understood that various modifications may be made without departing from the spirit and scope of the invention. For example, some of the steps described above may be order independent, and thus can be performed in an order different from that described.

The invention claimed is:

1. An automation method for preparing a blood sample for an examination, comprising:
preparing a fiber as test substrate, the fiber having a length suitable for the examination and a pre-selected width;
moving the fiber through a test liquid to coat the fiber with a sample test film of a desirable thickness, wherein the desirable thickness is uniform across the sample test film and is such that the test film contains only a single layer of blood cells, wherein the desirable thickness is controlled through a speed at which the fiber is pulled through the test liquid and by the pre-selected width; and
processing the fiber coated with the sample test film in preparation for examination.

2. The automation method of claim 1, wherein the fiber moves through the test liquid at a constant speed and the speed is calibrated such that the sample test film is of the desirable thickness.

3. The automation method of claim 1, wherein the processing of the sample test film in preparation for the examination comprises staining the sample test film with a staining solution.

4. The automation method of claim 1, wherein the preparing of the fiber as test substrate comprises pre-coating the fiber with a pre-coating solution.

5. The automation method of claim 1, further comprising:
moving the fiber through a microscope equipped with a digital camera;
examining the sample test film using the microscope; and
recording digital images of the sample test film using the digital camera.

6. The automation method of claim 1, further comprising applying the test liquid to the coated fiber using one of a pipette, a nozzle, a print head, and a spraying device, to ensure that the sample test film is of a uniform thickness.

7. An automation method for preparing a blood sample for an examination, comprising:

preparing a fiber as test substrate, the fiber having a length suitable for the examination;

spraying the fiber with a test liquid to coat the fiber with a sample test film of a desirable thickness, wherein the desirable thickness is uniform across the sample test film and is such that the test film contains only a single layer of blood cells, wherein the desirable thickness is controlled by controlling a speed at which the fiber is pulled through the test liquid; and processing the fiber coated with the sample test film in preparation for examination.

* * * * *